US00PP17853P2

(12) United States Plant Patent
Dekker

(10) Patent No.: US PP17,853 P2
(45) Date of Patent: Jul. 10, 2007

(54) ***CHRYSANTHEMUM* PLANT NAMED 'EUROBELLE GOLDEN'**

(50) Latin Name: *Chrysanthemum×morifolium*
Varietal Denomination: Eurobelle Golden

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 155 days.

(21) Appl. No.: 11/118,920

(22) Filed: Apr. 30, 2005

(51) Int. Cl.
*A01H 5/00* (2006.01)

(52) U.S. Cl. ..... Plt./289

(58) Field of Classification Search ..... Plt./289
See application file for complete search history.

(56) References Cited

U.S. PATENT DOCUMENTS

PP12,659 P2 * 5/2002 Dekker ..... Plt./288

* cited by examiner

*Primary Examiner*—Wendy Haas
(74) *Attorney, Agent, or Firm*—C. A. Whealy

(57) ABSTRACT

A new and distinct cultivar of *Chrysanthemum* plant named 'Eurobelle Golden', characterized by its decorative-type inflorescences with elliptic-shaped, dark golden yellow-colored florets; strong and upright flowering stems; freely flowering habit; early and uniform flowering response; and good postproduction longevity.

1 Drawing Sheet

Botanical designation: *Chrysanthemum×morifolium.*
Cultivar denomination: 'Eurobelle golden'.

BACKGROUND OF THE INVENTION

The present invention relates to a new and distinct cultivar of *Chrysanthemum* plant, botanically known as *Chrysanthemum×morifolium* and referred to by the name 'Eurobelle Golden'.

The new *Chrysanthemum* is a naturally-occurring whole plant mutation of the *Chrysanthemum×morifolium* cultivar Eurobelle Yellow, not patented. The new *Chrysanthemum* was discovered and selected by the Inventor in September, 2003 as a single flowering plant within a population of plants of the parent selection in a controlled environment in Hensbroek, The Netherlands.

Asexual reproduction of the new *Chrysanthemum* by terminal cuttings harvested in Hensbroek, The Netherlands since October, 2003, has shown that the unique features of this new *Chrysanthemum* are stable and reproduced true to type in successive generations.

BRIEF SUMMARY OF THE INVENTION

The cultivar Eurobelle Golden has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Eurobelle Golden'. These characteristics in combination distinguish 'Eurobelle Golden' as a new and distinct cultivar:

1. Decorative-type inflorescences with elliptic-shaped, dark golden yellow-colored ray florets; typically grown as a spray-type.
2. Strong and upright flowering stems.

3. Freely flowering habit.
4. Early and uniform flowering response.
5. Good postproduction longevity.

Plants of the new *Chrysanthemum* can be compared to plants of the parent, the cultivar Eurobelle Yellow. In side-by-side comparisons conducted in Hensbroek, The Netherlands, plants of the new *Chrysanthemum* differed from plants of the cultivar Eurobelle Yellow primarily in ray floret coloration as plants of the new *Chrysanthemum* have darker yellow-colored ray florets.

Plants of the new *Chrysanthemum* can be compared to plants of the *Chrysanthemum* cultivar Eurobelle, disclosed in U.S. Plant Pat. No. 12,659. In side-by-side comparisons conducted in Hensbroek, The Netherlands, plants of the new *Chrysanthemum* differed primarily from plants of the cultivar Eurobelle in the following characteristics:

1. Leaves of plants of the new *Chrysanthemum* and the cultivar Eurobelle differed in leaf shape.
2. Plants of the new *Chrysanthemum* had smaller inflorescences than plants of the cultivar Eurobelle.
3. Ray florets of plants of the new *Chrysanthemum* were flat whereas ray florets of plants of the cultivar Eurobelle were incurving.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph at the top of the sheet comprises a side perspective view of a typical flowering stem of 'Eurobelle Golden'.

The photograph at the bottom of the sheet comprises a close-up view of upper and lower surfaces of typical inflorescences and typical leaves of 'Eurobelle Golden'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown during the winter in Hensbroek, The Netherlands, under commercial practice in a glass-covered greenhouse. Plants were initially given long day/short night treatments followed by short day/long night treatments to induce flower initiation and development. During the production of the plants, day temperatures ranged from 17.5° C. to 30° C., night temperatures ranged from 18.5° C. to 24° C. and light levels were about five kilolux. Plants were pinched once and were about eleven weeks from planting when the photographs and the description were taken.

Botanical classification: *Chrysanthemum×morifolium* cultivar Eurobelle Golden.

Commercial classification: Decorative-type *Chrysanthemum* typically grown as a spray-type cut flower.

Parentage: Naturally-occurring whole plant mutation of the *Chrysanthemum×morifolium* 'Eurobelle Yellow', not patented.

Propagation:

*Type.*—Terminal tip cuttings.

*Time to initiate roots, summer.*—About 6 days at 20° C.

*Time to initiate roots, winter.*—About 7 days at 20° C.

*Time to produce a rooted cutting, summer.*—About 14 days at 20° C.

*Time to produce a rooted cutting, winter.*—About 16 days at 20° C.

*Root description.*—Fine and freely branching; light brown in color.

Plant description:

*Appearance.*—Herbaceous decorative-type cut *Chrysanthemum;* typically grown as a spray-type; erect and strong flowering stems. Vigorous growth habit.

*Flowering stem description.*—Length: About 70 to 80 cm. Diameter: About 6 mm. Strength: Strong. Texture: Pubescent. Aspect: Erect. Branching habit: Plants are typically grown as single stems. Color: 146B.

*Foliage description.*—Arrangement: Alternate. Length: About 9 to 12 cm. Width: About 5.5 to 7.5 cm. Apex: Acute. Base: Attenuate; asymmetrical. Margin: Palmately lobed. Texture, upper and lower surface: Pubescent; rough. Petiole length: About 2 to 3.5 cm. Color: Developing foliage, upper surface: 147A. Developing foliage, lower surface: Close to 147B. Fully expanded foliage, upper surface: 137A to 147A. Fully expanded foliage, lower surface: 147B. Venation, upper surface: 146A. Venation, lower surface: 146B. Petiole, upper and lower surfaces: 146B.

Inflorescence description:

*Appearance.*—Decorative-type inflorescence form with elliptic-shaped ray florets. Inflorescences borne on terminals above foliage. Disk and ray florets develop acropetally on a capitulum. Inflorescences not fragrant. Typically grown as a spray-type.

*Flowering response.*—Under natural conditions, plants typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 7.5 weeks later. Early and uniform flowering response.

*Postproduction longevity.*—Cut inflorescences will maintain good substance and form for about three weeks.

*Quantity of inflorescences per flowering stem.*—About 10 to 18 inflorescences per flowering stem.

*Inflorescence size.*—Diameter: About 5 to 6 cm. Depth (height): About 2 to 3 cm. Diameter of disc: About 6 mm.

*Inflorescence buds.*—Height: About 8 to 10 mm. Diameter: About 1 to 1.3 cm. Shape: Spherical. Color: 137B to 137C.

*Ray florets.*—Length: About 1.1 to 3.3 cm. Width: About 1 to 10 mm. Shape: Elliptic; flat. Apex: Praemorse. Base: Cuneate to fused. Margin: Entire. Texture, upper and lower surfaces: Smooth, glabrous. Number of ray florets per inflorescence: About 190 in numerous whorls. Color: When opening, upper surface: 7B blushed with 26A. When opening, lower surface: 10B. Fully opened, upper surface: 5B blushed with 22A; color becoming closer to 7C with development. Fully opened, lower surface: 8C.

*Disc florets.*—Shape: Tubular; elongated. Length: About 5 mm. Width: About 1 to 2 mm. Number of disc florets per inflorescence: About 14. Color: Immature: 145A to 145B. Mature: Apex: 144A. Mid-section 14C. Base: 150D.

*Peduncles.*—Length, terminal peduncle: About 6.5 cm. Length, fourth peduncle: About 12.5 cm. Diameter: About 2 to 3 mm. Angle: About 60° C. from vertical. Strength: Strong. Texture: Pubescent. Color: 146A.

*Reproductive organs.*—Androecium: Present on disc florets only. Anther color: Close to 151B. Pollen: None observed. Gynoecium: Present on both ray and disc florets. Stigma length: About 1 mm. Stigma diameter: About 0.3 mm. Stigma color: Close to 151B.

*Seed/fruit.*—Seed and fruit production has not been observed.

Disease/pest resistance: Resistance to known *Chrysanthemum* pathogens and pests has not been observed on plants of the new *Chrysanthemum.*

It is claimed:

1. A new and distinct cultivar of *Chrysanthemum* plant named 'Eurobelle Golden', as illustrated and described.

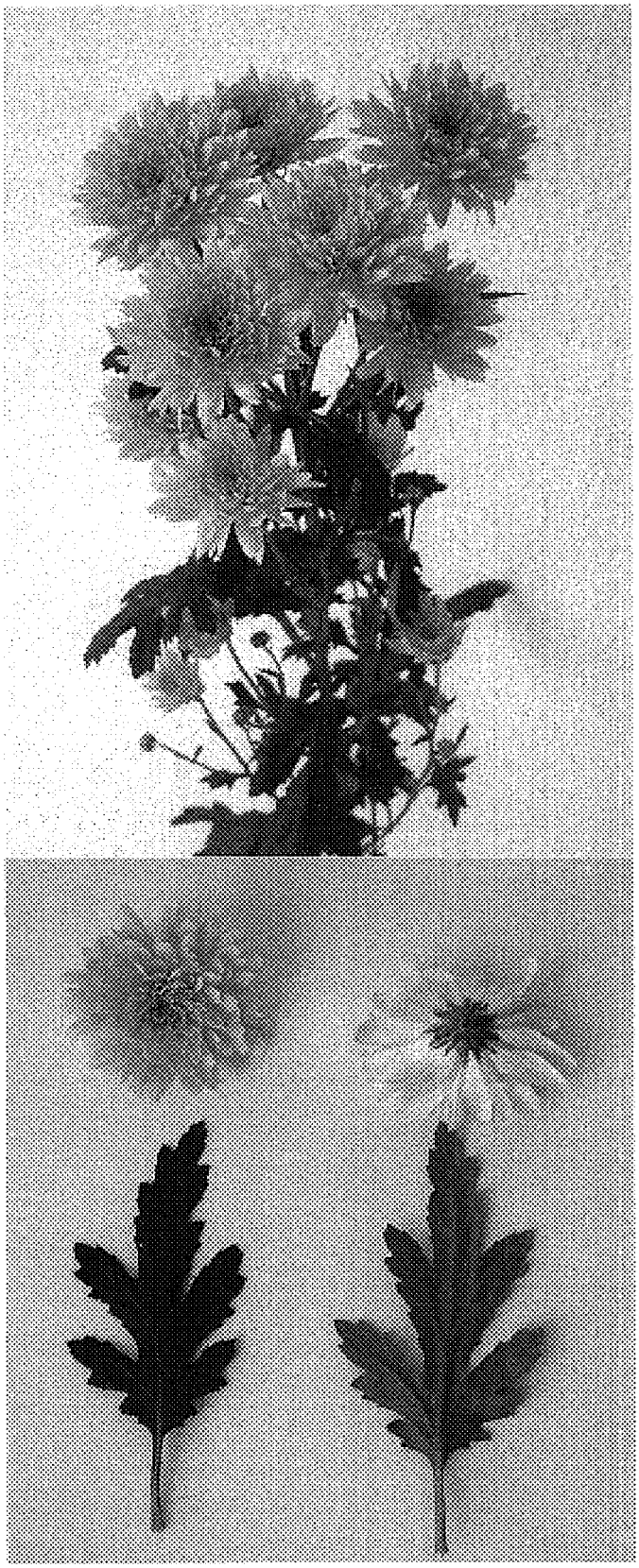

* * * * *